United States Patent
Lange et al.

[11] Patent Number: 6,012,316
[45] Date of Patent: Jan. 11, 2000

[54] PROCESS FOR INCREASING THE LIFESPAN OF DENTAL COMPONENTS

[75] Inventors: Gerlinde Lange, Langenselbold; Franz-Josef Grau, Neunkirchen am Brand, both of Germany

[73] Assignee: Degussa Aktiengesellschaft, Frankfurt am Main 1, Germany

[21] Appl. No.: 08/924,661

[22] Filed: Sep. 5, 1997

[30] Foreign Application Priority Data

Sep. 6, 1996 [DE] Germany ............ 196 36 215

[51] Int. Cl.⁷ ................ B21J 51/28; B24C 1/00
[52] U.S. Cl. ........................ 72/53; 451/38
[58] Field of Search ............. 72/53; 451/38, 451/39

[56] References Cited

U.S. PATENT DOCUMENTS

| | | | |
|---|---|---|---|
| 3,073,022 | 1/1963 | Bush et al. | 72/53 |
| 3,410,124 | 11/1968 | Suwa | 72/53 |
| 3,754,976 | 8/1973 | Babecki et al. | 72/53 |
| 4,034,585 | 7/1977 | Straub | 72/53 |
| 4,475,370 | 10/1984 | Stark et al. | 72/53 |
| 5,251,468 | 10/1993 | Lin et al. | 72/53 |
| 5,697,265 | 12/1997 | McComber et al. | 72/53 |
| 5,704,239 | 1/1998 | Beals et al. | 72/53 |

FOREIGN PATENT DOCUMENTS

| | | |
|---|---|---|
| 83 13 563 | 3/1986 | Germany . |
| 43 11 319 | 10/1993 | Germany . |
| 01854627 | 9/1985 | Japan .............. 72/53 |

OTHER PUBLICATIONS

Metals Handbook, 8th Edition, vol. 2. Heat treating, Cleaning, and Finishing, American Society for Metals, pp. 398–405, 1964.

Primary Examiner—David Jones
Attorney, Agent, or Firm—Smith, Gambrell & Russell, LLP

[57] ABSTRACT

With a view to increasing the lifespan of metallic dental components as regards fatigue fractures, compressive stresses are introduced into the surface layer of these components, such as by means of shot-peening.

8 Claims, 3 Drawing Sheets

PROCESS FOR INCREASING THE LIFESPAN OF DENTAL COMPONENTS

INTRODUCTION AND BACKGROUND

The present invention relates to a process for increasing the lifespan of metallic dental components such as root pins, implants, prostheses or bridges by means of a surface treatment of these components. In a further aspect, the present invention also relates to products produced by the foregoing process.

Metallic components generally cannot endure frequent random vibratory loads without undergoing fracture, even when the stress amplitude is relatively small in relation to the tensile strength of the corresponding materials as ascertained in a tensile test. Metallic components also often undergo fracture when the stress amplitude is smaller than the strain limit of the material employed. The behavior of the material is accordingly determined by the stress amplitude and the frequency of its repetition. In addition, the environmental conditions and the geometry of the components also have an effect on the fatigue strength under vibratory stress.

In the field of dentistry many components are intentionally (e.g., spring pins) or unintentionally (e.g., root pins) subjected to vibratory stress. Time and time again this results in the problem that components—although manufactured from an optimized alloy and adequately dimensioned, such as root pins or structural elements for example—fracture without material defects or processing faults subsequently being detectable. Investigations show rather that the components have failed by reason of material fatigue, which is further promoted by the environmental conditions in the mouth; e.g. exposure to saliva. One way of avoiding these fatigue fractures would be a greater dimensioning of the components in order to reduce the local stresses in the component. However, for reasons relating to the space situation in the mouth or for aesthetic reasons, this is often not possible. Such fractures can mostly be repaired only with great difficulty and considerable effort.

In vehicle and aircraft construction, shot-peening for improving the physical properties of metal objects has been known for many years and is employed successfully in these fields. The details of such techniques are described in many text books. For instance, it has generally been found that in respect of many components that have been subjected to shot-peening it has been possible to detect an increased fatigue strength. The increased fatigue strength in these cases is to be ascribed to the compressive stresses introduced into the surface layer which hinder the formation of cracks in the component. Thus in the field of vehicle construction, differential gears for vehicle axles, spindles, shafts, thrust collars and also connecting rods are shot-peened in order to increase their endurance strength. Also in the field of turbine construction, vanes that are utilized in the compressor part of the turbine are often shot-peened in order to increase the fatigue strength and hence the lifespan of the component.

Such techniques have not hitherto been adopted in the dental field. Neither have special processes for improving fatigue strength hitherto been taken into consideration.

Sand-blasting is employed in the dental field for the cleaning of castings, for example. However, as a result of the sand-blasting the quantity of material eroded is greater than the amount of deformation introduced into the surface layer. The surface of the components is therefore only roughed up. Since they are not overlaid by compressive stresses, these microscopic defects lead instead to a decrease in the fatigue strength of these components.

It was therefore an object of the present invention to develop a process for increasing the lifespan of metallic dental components such as root pins, implants, prostheses or bridges by means of a surface treatment without encountering the disadvantages of prior known strengthening techniques used in dental technology.

SUMMARY OF THE INVENTION

In achieving the above and other objects, a feature of the present invention resides in introducing compressive stresses into the surface layer of a metallic dental component by means of mechanical influences.

A further feature of the invention resides in forming these compressive stresses into the surface layer of the metallic dental components by means of shot-peening.

BRIEF DESCRIPTION OF DRAWINGS

The present invention will be further understood with reference to the drawings, wherein.

DETAILED DESCRIPTION OF INVENTION

Surprisingly it has been shown that the lifespan of components manufactured from conventional dental alloys increases considerably as a result of introducing compressive stresses into the surface layer of the components by means of shot-peening, so that the number of alternations of load until fracture occurs can increase by more than two powers of ten. The points of indentation remaining on the surface of the shot-peened components can either be removed by suitable means, without neutralization of the compressive stresses in the surface layer, or, with a view to increasing the retention—e.g., in the case of root pins—they can be left. An increase in the fatigue strength cannot be achieved by sand-blasting the components.

In carrying out the process of this invention, a variety of types of pellets can be used for the shot-peening operation, glass beads, titanium pellets, steel pellets and ceramic pellets have been found to be particularly good. The size of the pellets and beads can be adjusted depending upon the size of the dental component. Since the dental components are relatively small objects, the size of the pellets used for shot-peening is determined based on routine experimentation by persons skilled in the art. In order to keep a good control on the quality of the final product and to insure that surface roughness will be as low as possible, the type of shot material should be spherical in shape. All types of shot can be used provided that the abraded material will not be injurious to health.

To determine when sufficient treatment of dental components is achieved, the optimum parameters are determined by a series of measurements. A plot is then created of life-time versus shot peening intensity. The results obtained, of course, depend on the type of shot material and the type of material of which the dental component is made.

Figure 1:
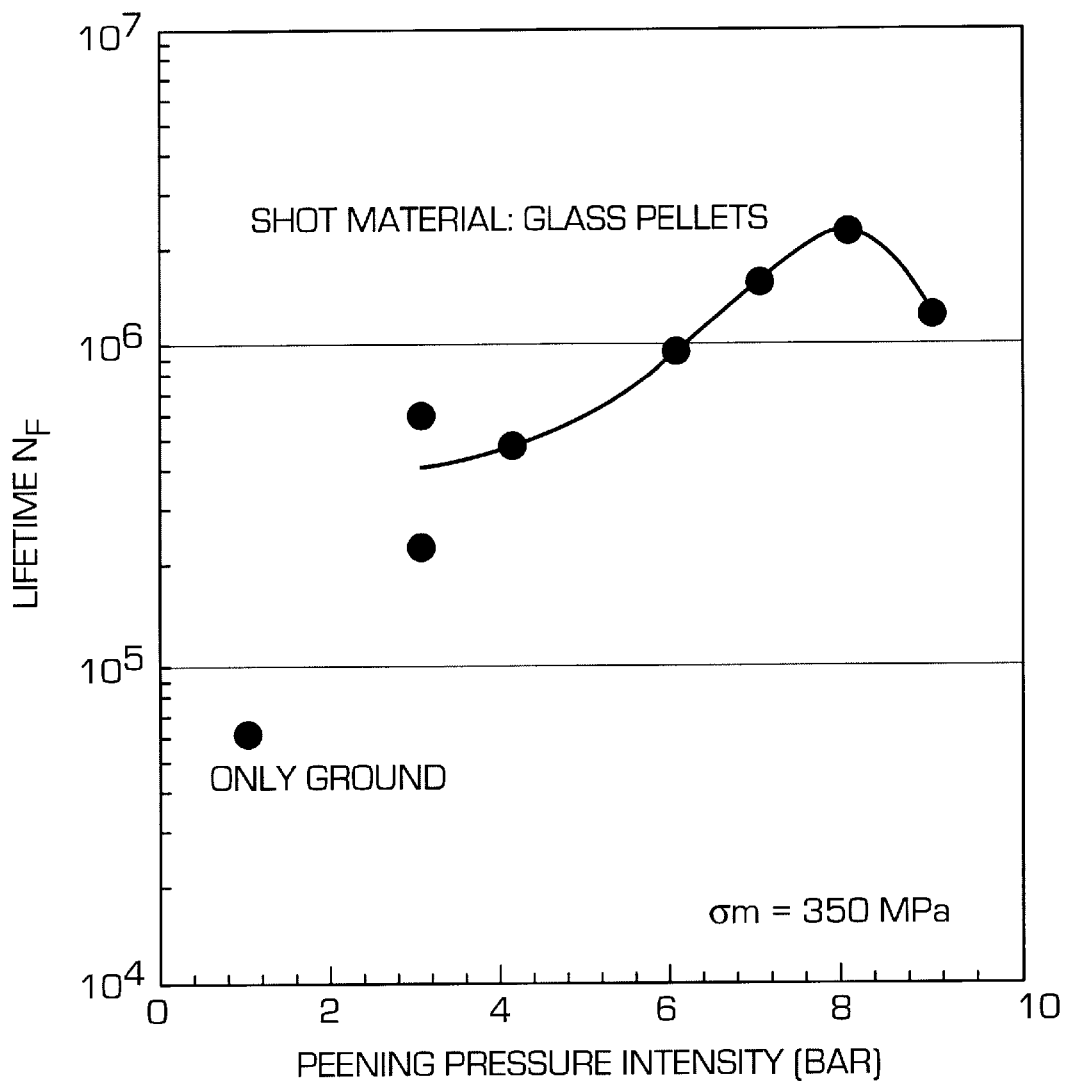
FIG. 1 is a plot of lifetime of a dental component versus peening pressure intensity.

An example of such a plot is shown in FIG. 1. The stress imposed in this sample was 350 MPa using a dental component made of Permador® and the shot was glass pellets. The results plotted clearly demonstrate that a longer lifetime was obtained by shot-peening compared with a specimen which was subject to grinding.

The following examples are intended to illustrate the invention in more detail:

Examples

Test rods having dimensions 40 mm in length and 2.5 mm in diameter and consisting of various materials were shot-peened with glass beads having a granulation of 420 to 590 μm. The pressure of the jet amounted to 0.7 MPa with a nozzle-to-specimen spacing of 35 mm and a shot-peening-time of 45 seconds. In the process the specimen rotated about its axis once per second.

With a view to appraising the lifespan or endurance strength of these specimens, so-called Wöhler curves were determined. To this end, several test rods made of the same material are subjected to vibratory stress at constant mean stress with various large stress amplitudes until fracture occurs.

Figure 2:
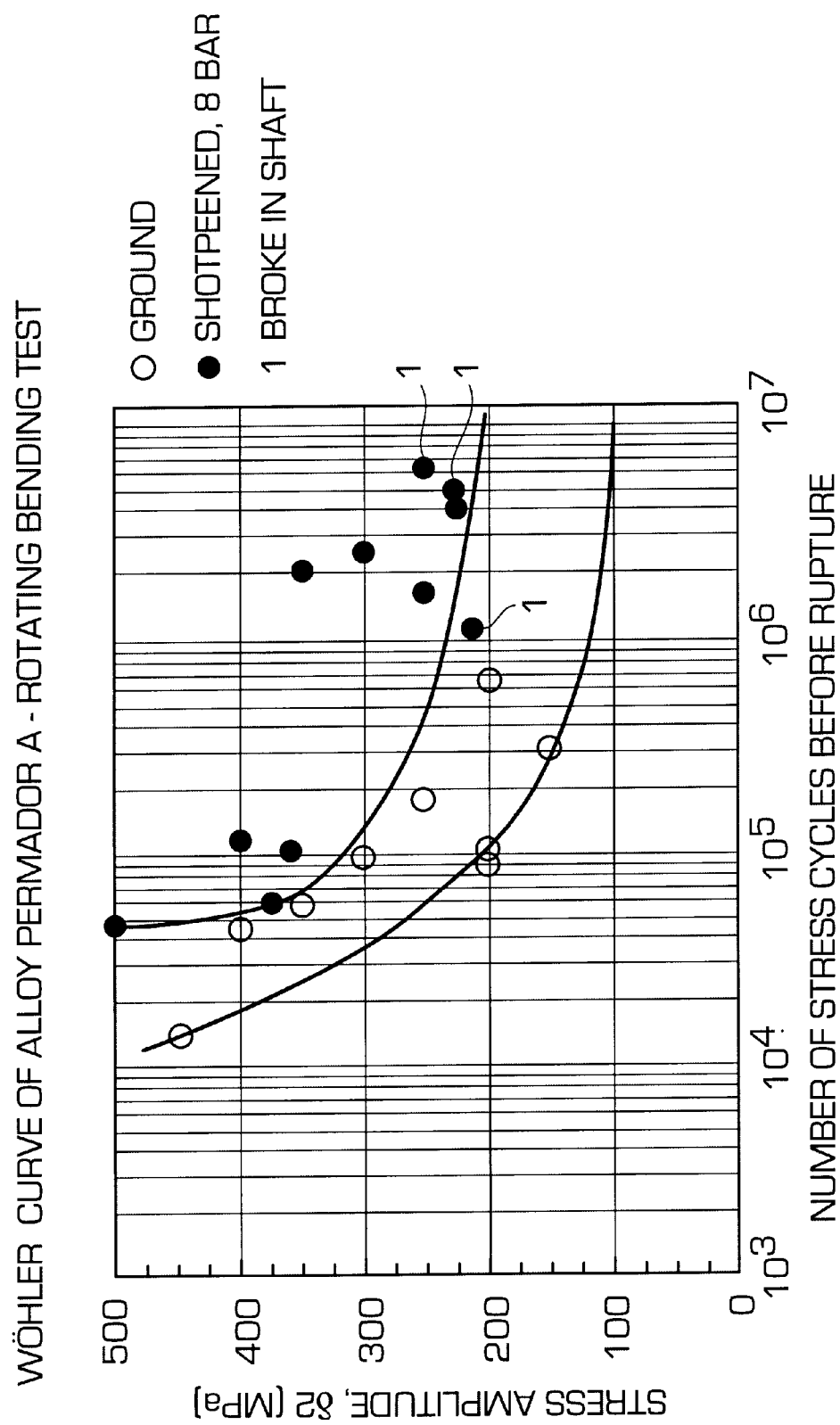
FIG. 2 is a Wöhler curve obtained by carrying out the present invention.

The results obtained can be plotted on a Wöhler curve as shown in FIG. 2 and will depend on the shot, the pressure and the type of dental component. FIG. 2 was obtained from a specimen of Permador® dental component using glass pellets and a peening-pressure of 8 bar.

With regard to ranges of conditions for the shot-peening process of the invention the following table shows suitable conditions:

|  | range, which can be used | preferred range |
| --- | --- | --- |
| inner nozzle diameter | 3 ... 8 mm | 7 mm |
| distance nozzle - sample | 10 ... 40 mm | 35 mm |
| peening pressure (injector type) | 1 to 10 bar | 2 ... 9 bar |
| revolutions time | 0.5 ... 5 (1/s) | 1 (1/s) |
| exposure time | 30 ... 60 sec. | 45 sec. |

Figure 3:
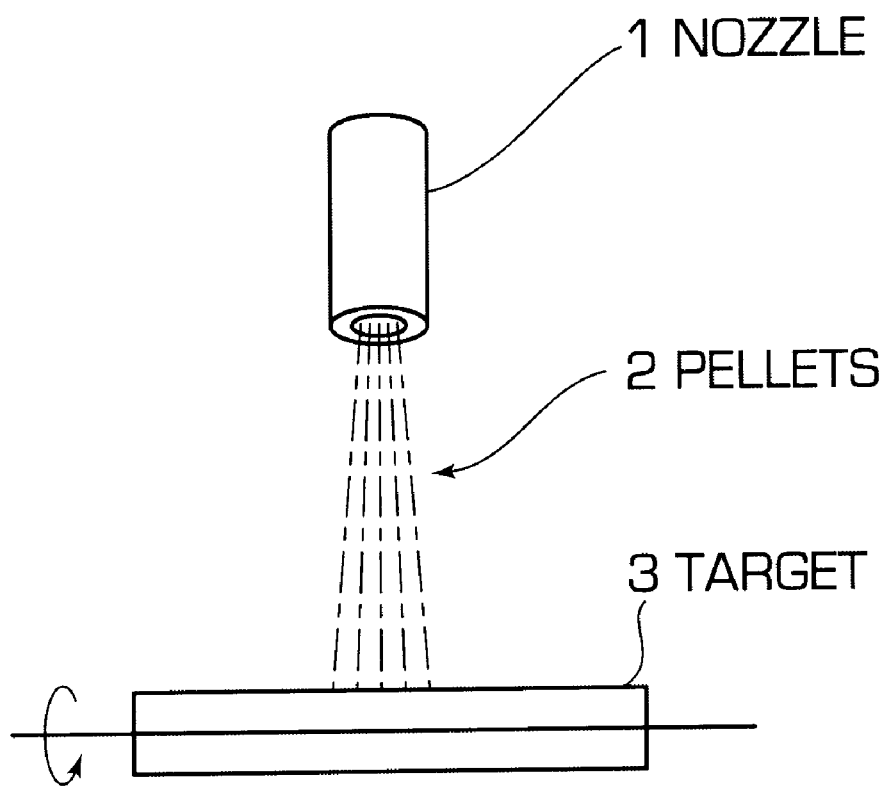
FIG. 3 is a schematic view of the apparatus used according to the invention.

FIG. 3 shows the simplified representation of a suitable shot peening apparatus including nozzle 1 impinging pellets 2 onto the dental component 3. The target or dental component is rotated to obtain uniform treatment.

The following Table shows the values measured in respect of the shot-peened specimens in comparison with those of untreated specimens, for three materials. The considerable increase in the endurance strengths or lifespan of the shot-peened specimens in relation to the untreated specimens can be seen.

Further modifications and variations of the foregoing will be apparent to those skilled in the art and are intended to be encompassed by the claims appended hereto.

German priority application 196 36 215.6 is relied on and incorporated herein by reference.

Table of Examples:

| Material | Proof stress applied (MPa) | Alternations of load until fracture | |
| --- | --- | --- | --- |
| | | Untreated specimens | Shot-peened specimens |
| Example 1 | 200 | 89,000 | >11,000,000 |
| 60 Au, 24.9 Pt, | 300 | 100,000 | 2,600,000 |
| 15 Pd, 0.1 Ir | 350 | 61,000 | 2,200,000 |
| Example 2 | 300 | 20,000 | >10,000,000 |
| Titanium | 350 | 10,000 | 300,000 |
| | 400 | 8,000 | 290,000 |
| Example 3 | 150 | 530,000 | >10,000,000 |
| 60 Pt, 40 Au | 200 | 450,000 | 8,300,000 |
| | 250 | 120,000 | 4,000,000 |
| | 300 | 85,000 | 2,500,000 |
| | 400 | 27,000 | 210,000 |

We claim:

1. A process for increasing the lifespan of a metallic dental component comprising forming compressive stresses into a surface layer of said component wherein said compressive stresses are introduced by shot peening said surface and wherein said shot peening is performed with a jet spaced 10 to 40 mm from said component and wherein said shot peening uses a pressure of from 1 to 10 bar and is carried out for 30 to 60 seconds.

2. The process according to claim 1 where said metallic dental component is a member selected from the group consisting of root pin, implant, prosthesis and bridge.

3. The process according to claim 1 wherein said component is exposed to a jet of finely divided pellets at a sufficient pressure and for a sufficient time to impart compressive stresses into the surface layer to thereby increase the number of flexures the said component can undergo before fracture compared to a component that has not been exposed to shot-peening.

4. The process according to claim 3 wherein said pellets are selected from the group consisting of glass, steel, titanium and ceramic pellets.

5. The process according to claim 1 wherein said component is exposed to a jet of glass beads having a size of 420 to 590 μm at a pressure of 0.7 Mpa for at least 45 seconds.

6. The process according to claim 1 wherein the pressure of peening is 2 to 9 bar.

7. The process according to claim 1 wherein the jet is spaced 35 mm from said dental component.

8. A process for increasing the lifespan of a metallic dental component comprising forming compressive stresses into a surface layer of said component wherein said compressive stresses are introduced by shot peening said surface and wherein said shot peening is performed with a jet having a diameter of from 3 to 8 mm and is spaced 10 to 40 mm from said component and wherein said shot peening uses a pressure of from 1 to 10 bar and is carried out for 30 to 60 seconds.

* * * * *

UNITED STATES PATENT AND TRADEMARK OFFICE
CERTIFICATE OF CORRECTION

PATENT NO.     : 6,012,316
DATED          : January 11, 2000
INVENTOR(S)    : Gerlinde Lange et al.

It is certified that error appears in the above-identified patent and that said Letters Patent is hereby corrected as shown below:

<u>Title page</u>,
Item [75], inventors, add -- Jürgen Kiese --.

Signed and Sealed this

Twenty-third Day of July, 2002

Attest:

Attesting Officer

JAMES E. ROGAN
*Director of the United States Patent and Trademark Office*